(12) United States Patent
Webster

(10) Patent No.: US 12,102,555 B2
(45) Date of Patent: Oct. 1, 2024

(54) ORAL APPLIANCE

(71) Applicant: Sleeping Well LLC, Shelburne, VT (US)

(72) Inventor: Daniel Webster, Shelburne, VT (US)

(73) Assignee: Sleeping Well Inc., Shelburne, VT (US)

( * ) Notice: Subject to any disclaimer, the term of this patent is extended or adjusted under 35 U.S.C. 154(b) by 333 days.

(21) Appl. No.: 17/400,238

(22) Filed: Aug. 12, 2021

(65) Prior Publication Data

US 2022/0054301 A1 Feb. 24, 2022

Related U.S. Application Data

(60) Provisional application No. 63/069,289, filed on Aug. 24, 2020.

(51) Int. Cl.
*A61F 5/56* (2006.01)
(52) U.S. Cl.
CPC ........ *A61F 5/566* (2013.01); *A61F 2005/563* (2013.01)
(58) Field of Classification Search
CPC ................ A61F 5/566; A61F 2005/563; A61F 2002/30991; A61F 2/2803; A61F 5/56; A61B 13/00; A61B 5/1072; A61B 5/1076; A61B 5/481; A61B 17/8071; A61B 5/4812; A61B 5/4818; A61B 5/4557; A61B 5/097; A63B 2071/086; A63B 71/085; A61C 19/045; A61C 11/00; A61C 7/08; A61C 7/10; A61C 7/36; A61C 9/0006; Y10S 602/902

USPC .......................................................... 128/848
See application file for complete search history.

(56) References Cited

U.S. PATENT DOCUMENTS

| | | | |
|---|---|---|---|
| 3,536,069 A | 10/1970 | Gores | |
| 5,194,003 A | 3/1993 | Garay | |
| 5,570,704 A | 11/1996 | Buzzard | |
| 5,794,627 A | 8/1998 | Frantz | |
| 5,947,724 A * | 9/1999 | Frantz | A61F 5/566 |
| | | | 128/848 |
| 7,730,891 B2 | 6/2010 | Lamberg | |
| 8,104,467 B2 | 1/2012 | Napier | |
| 8,113,206 B2 | 2/2012 | Roettger | |
| 8,567,408 B2 | 10/2013 | Roettger | |

(Continued)

FOREIGN PATENT DOCUMENTS

| | | | | |
|---|---|---|---|---|
| FR | 2863863 A1 * | 6/2005 | ............ | A61C 7/08 |
| JP | H11508472 * | 7/1999 | ............ | A61C 7/08 |

*Primary Examiner* — Ophelia A Hawthorne
*Assistant Examiner* — Michael Milo

(57) ABSTRACT

An oral appliance that is placed in a user's mouth. An upper tray is designed to engage with a user's maxillary teeth, and a lower tray is designed to engage with a user's mandibular teeth. Thermal impression material may be designed into at least one of the trays to engage the upper and lower dentition. Two side straps mechanisms are designed to connect the upper and lower trays, and may provide forward positioning of the lower jaw relative to the upper jaw. A ramped lingual shelf may be included on the inside portion of the lower tray, to position a user's tongue forward and upward. The upper tray has an open section in its anterior portion which provides additional space for a forward-positioned tongue. Upper and lower trays may be constructed out of rigid polypropylene or similar materials.

21 Claims, 7 Drawing Sheets

(56) References Cited

U.S. PATENT DOCUMENTS

| | | | |
|---|---|---|---|
| 8,783,259 B2 | 7/2014 | Spencer | |
| 8,833,374 B2 | 9/2014 | Fallon | |
| 8,881,733 B1 | 11/2014 | Harkins | |
| 9,949,867 B2 | 4/2018 | Veis | |
| 10,328,225 B2 | 6/2019 | Garner | |
| 10,945,818 B1* | 3/2021 | Motlagh | A61C 7/08 |
| 2006/0008778 A1* | 1/2006 | Rosenberg | A45D 44/22 |
| | | | 433/229 |
| 2009/0308403 A1* | 12/2009 | Roettger | A61F 5/566 |
| | | | 433/213 |
| 2010/0043804 A1 | 2/2010 | Razmovski | |
| 2010/0083971 A1 | 4/2010 | Webster | |
| 2011/0000495 A1* | 1/2011 | Ash | A61F 5/566 |
| | | | 128/848 |
| 2011/0174319 A1* | 7/2011 | Busciglio | A61F 5/566 |
| | | | 128/862 |
| 2011/0226261 A1 | 9/2011 | Hernandez | |
| 2012/0073582 A1* | 3/2012 | Kopp | A61F 5/566 |
| | | | 128/848 |
| 2013/0112210 A1 | 5/2013 | Stein | |
| 2014/0283848 A1 | 9/2014 | Crichigno | |
| 2014/0326253 A1* | 11/2014 | Baratier | A61F 5/566 |
| | | | 382/128 |
| 2015/0079530 A1* | 3/2015 | Bergersen | A61F 5/566 |
| | | | 433/24 |
| 2015/0173935 A1 | 6/2015 | Cooper | |
| 2017/0151086 A1* | 6/2017 | Fareid | A61F 5/566 |
| 2018/0078405 A1 | 3/2018 | Farrell | |
| 2018/0207022 A1 | 7/2018 | Alvarez | |
| 2019/0117442 A1 | 4/2019 | Chodorow | |
| 2019/0175388 A1* | 6/2019 | Urban | A61F 5/566 |
| 2019/0374734 A1 | 8/2019 | Garner | |
| 2020/0061440 A1 | 2/2020 | Knutzen | |
| 2020/0069397 A1 | 3/2020 | Raslambekov | |

* cited by examiner

ORAL APPLIANCE

CROSS-REFERENCE TO RELATED APPLICATION

This application claims the priority of provisional application 63/069,289, filed 24 Aug. 2020

FEDERALLY-SPONSORED RESEARCH

None

BACKGROUND

This application relates to oral appliances.

SUMMARY

In an embodiment, there may be an oral appliance that includes: an upper tray with a first upper section, a second upper section, a first upper inner wall, a second upper inner wall, an upper outer wall; an anterior bridge connecting the first upper section to the second upper section, creating an open section between the first upper section and the second upper section; a lower tray with a first lower section, a second lower section, a first lower inner wall, a second lower inner wall, a first lower outer wall, a second lower outer wall; a lower bridge connecting the first lower section to the second lower section a first upper post located the first upper section; a second upper post located on the second upper section; a first lower post located on the first lower section; a second lower post located on the second lower section; a first side strap removably connecting the first upper post to the first lower post; and a second side strap removably connecting the second upper post to the second lower post, the first and second side straps a paired set identical in length to one another.

In an embodiment, there may be thermal impression material included on a surface that faces dorsal dental surfaces of each of the first upper section, the second upper section, the first lower section, and the second lower section. In an embodiment, there may be a first lower section and second lower section that each includes a lingual surface designed to engage a user's tongue. In an embodiment, there may be lingual surfaces of the first lower section and the second lower section further that each includes a lingual ramp with an inclined surface. In an embodiment, there may be a lower bridge ramped to match and connect the inclined surface of the lingual ramps on the first lower section and the second lower section. In an embodiment, there may be lingual ramps of the first lower section and the lingual ramp of the second lower section that promote forward and upward movement of a user's tongue.

In an embodiment, there may be a first upper post located on a first outer posterior portion of the first upper section; a second upper post located on a second outer posterior portion of the second upper section; a first lower post located on a first outer anterior portion of the first lower section; and a second lower post located on a second outer anterior portion of the second lower section. In an embodiment, there may be a first upper post located on a first outer anterior portion of the first upper section; a second upper post located on a second outer anterior portion of the second upper section; a first lower post located on a first outer posterior portion of the first lower section; and a second lower post located on a second outer posterior portion of the second lower section.

In an embodiment, the oral appliance may be designed to advance a user's mandible. In an embodiment, oral appliance may be designed such that the anterior bridge does not contact a user's anterior maxillary teeth when positioned in a user's mouth. In an embodiment, the oral appliance may be designed such that the lower bridge does not contact a user's anterior mandibular teeth when positioned in a user's mouth. In an embodiment, the oral appliance may be designed to provide a variable offset by swapping the paired set of first and second side straps for a different length paired set of first and second straps. In an embodiment, the open section may be designed into the oral appliance's anterior portion by the open anterior configurations of both the lower tray and the upper tray. In an embodiment, there may be a platform on an upper surface of the lower tray that creates a vertical space between the upper tray and the lower tray. In an embodiment, there may be a platform on a lower surface of the upper tray that creates a vertical space between the upper tray and the lower tray.

DESCRIPTION

The present application is in the field of oral appliances. In an embodiment, a device enables mandibular advancement. Advancing the position of the mandibular mouth structure relative to the position of the maxillary mouth structure is known as a method of reducing snoring and sleep apnea by reducing the restriction of the flow of air through the pharyngeal passageway. The decrease in air flow restriction causes a reduction in the vibration of soft tissue that's a cause of snoring, as well as reducing occlusion that's a cause of sleep apnea. In an embodiment, the device of the present application may be used in protecting the teeth from impact in athletic or work environments which necessitate the need for dental protection. In an embodiment, the device of the present application may be used as a bite guard to reduce the effects of bruxism. Some embodiments may not include a mandibular advancement feature.

When used in the treatment of snoring and/or obstructive sleep apnea, an oral appliance may be designed to advance the mandible. An effect of mandibular advancement is the protrusion of the lower jaw, thereby widening the upper airway to decrease air turbulence, a causative factor in snoring.

The device of the present disclosure may: separate upper and lower dental trays; use thermal impression material to engage the upper and lower dentition; include mechanisms to connect the upper and lower trays; and when desired, provides forward positioning of the lower jaw relative to the upper jaw. The design allows the maintenance of the desired positioning of the lower jaw while allowing minor sagittal and vertical movement.

Figure 1:
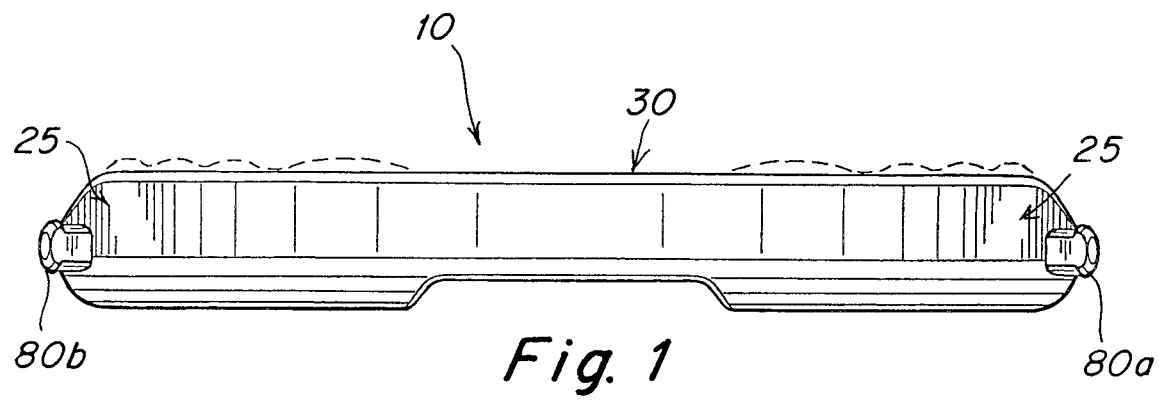
FIG. 1 is a front elevation view of an upper tray of an oral appliance.
Figure 2:
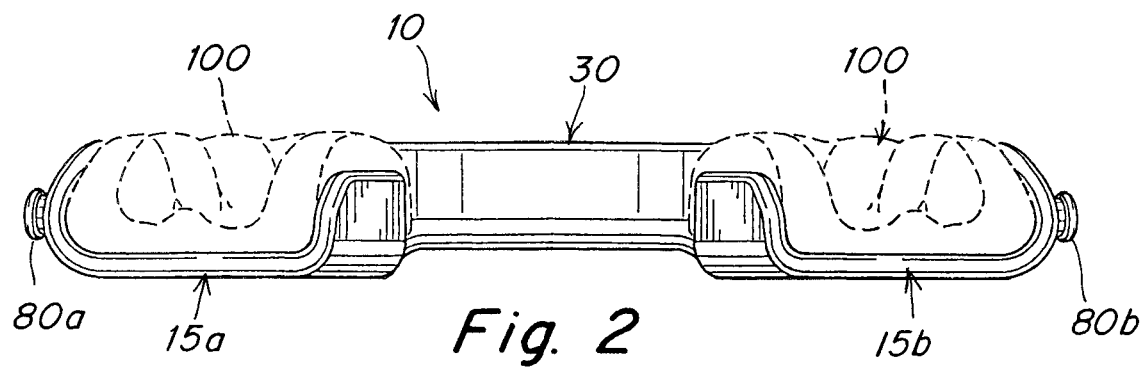
FIG. 2 is a back elevation view of an upper tray thereof.
Figure 3:
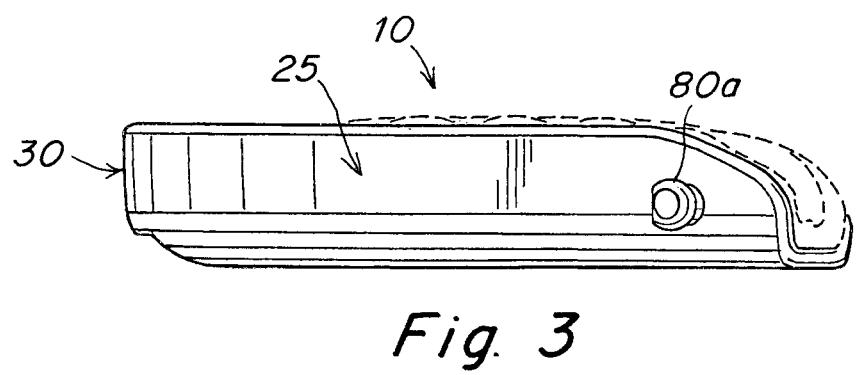
FIG. 3 is a right side elevational view of an upper tray, the left side being a mirror image thereof.

The oral appliance of the present application may include an upper tray and a lower tray, which are joined by two side straps, with further detail explained with reference to the accompanying drawings. The upper and lower trays may both be constructed out of a rigid polypropylene material, and other materials may be used as well. Throughout, the term anterior refers to the area closest to the front of a user's mouth, and therefore the front of the overall device; the term posterior refers to the rear of user's mouth, and therefore the rear of the overall device. The right side of the oral appliance is as seen in drawings such as FIG. 3, which shows a right side elevation view of the upper tray. The right side of the oral appliance is positioned in the left side of user's mouth, as is readily seen in FIG. 16.

Figure 13:
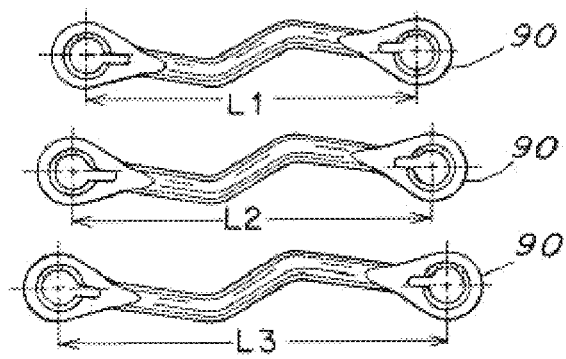
FIG. 13 is a side elevation view of three different length side straps.

FIGS. 1-5 show views of an upper tray, with FIGS. 6-11 showing views of a lower tray, and FIG. 13 showing examples of side straps. Referring to FIG. 1-5, upper tray 10 includes first upper section 15a, on which first upper inner wall 20a is positioned; and second upper section 15b, on which second upper inner wall 20b is positioned. Anterior bridge 30 is the front-most portion of upper outer wall 25, which forms a continuous surface that joins first upper section 15a to second upper section 15b, with sections 15a and 15b forming mirror images of each other.

Figure 4:
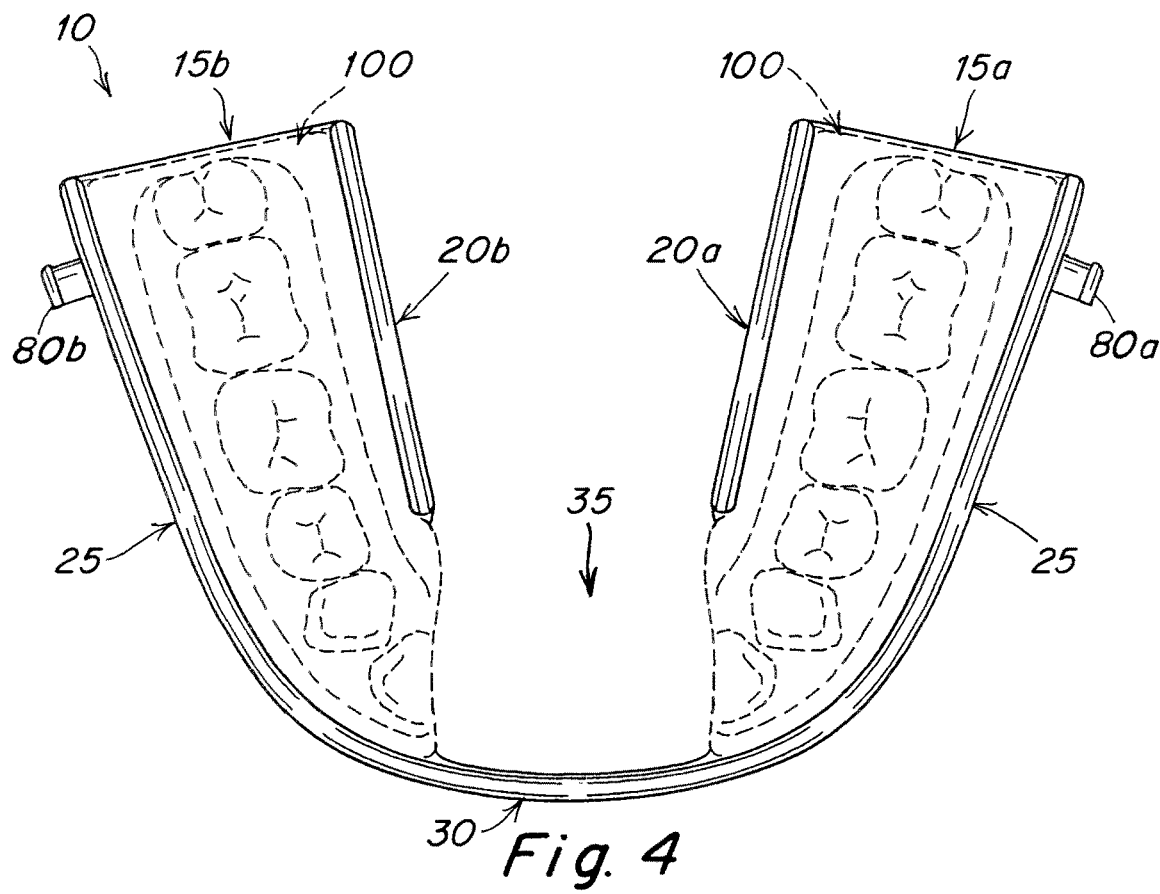
FIG. 4 is a top plan view of an upper tray.
Figure 5:
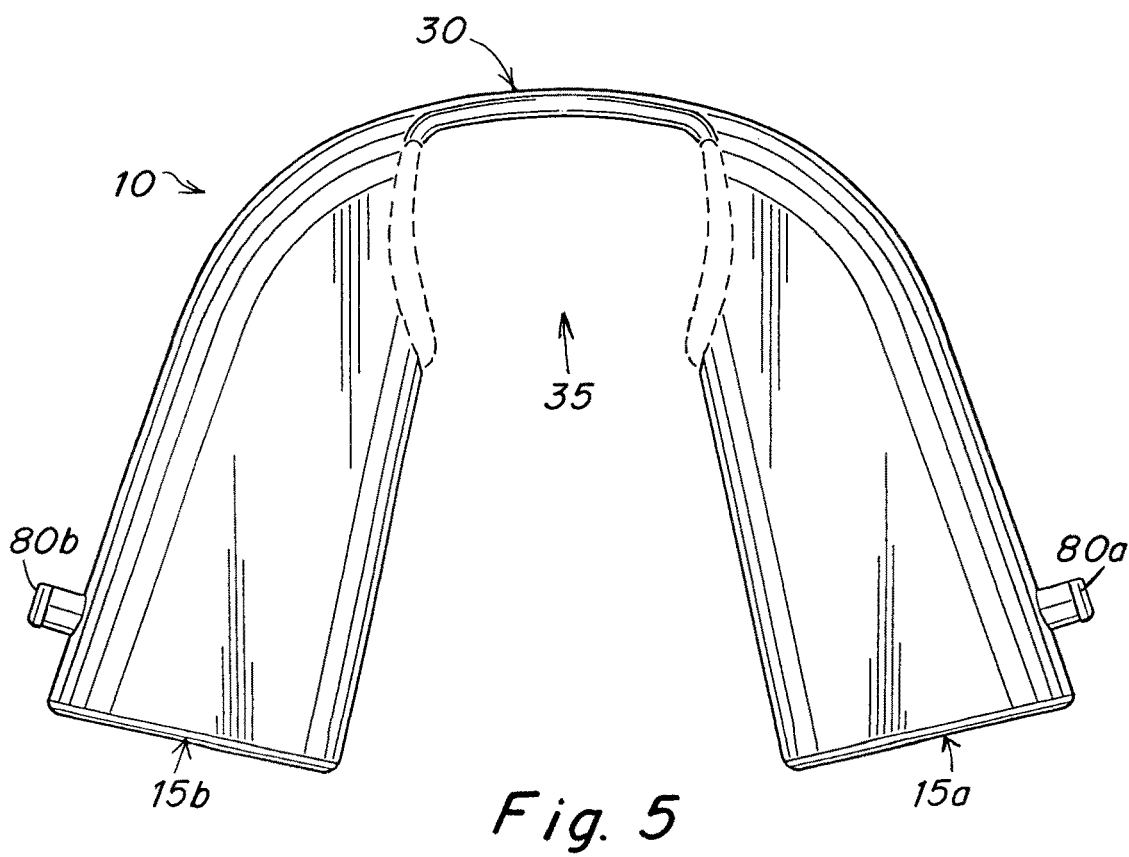
FIG. 5 is a bottom plan view of an upper tray.

FIGS. 4-5 show open section 35, which is the open area between the first upper section 15a and the second upper section 15b. Open section 35 creates interior space for the tongue to come forward, as will be further detailed. Also seen in FIGS. 1-5 is first upper post 80a, on the outer posterior portion of first upper section 15a, and second upper post 80b, on the outer posterior portion of second upper section 15b. Posts 80a and 80b may be used to removably anchor side straps 90, as seen in FIG. 13, as will be further detailed.

Figure 6:
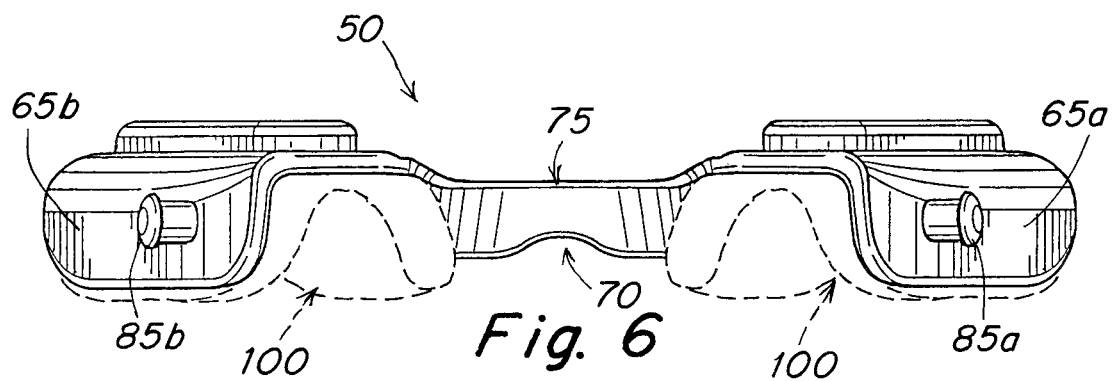
FIG. 6 is a front elevation view of a lower tray of an oral appliance.
Figure 7:
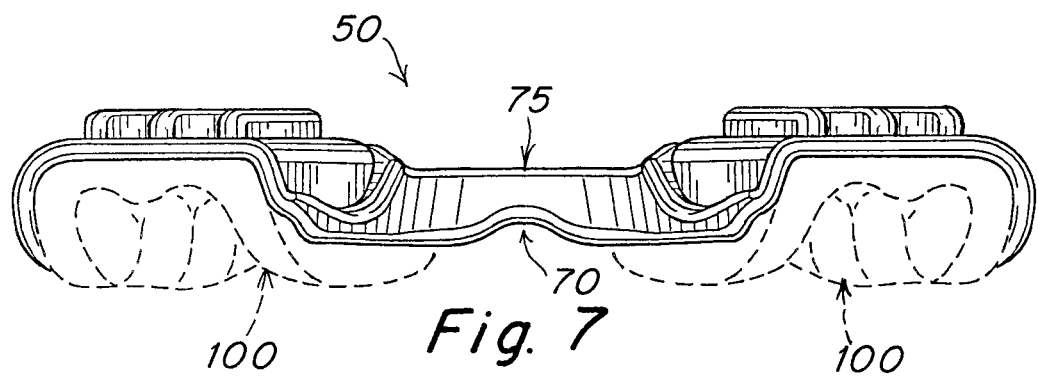
FIG. 7 is a back elevation view of a lower tray thereof.
Figure 8:
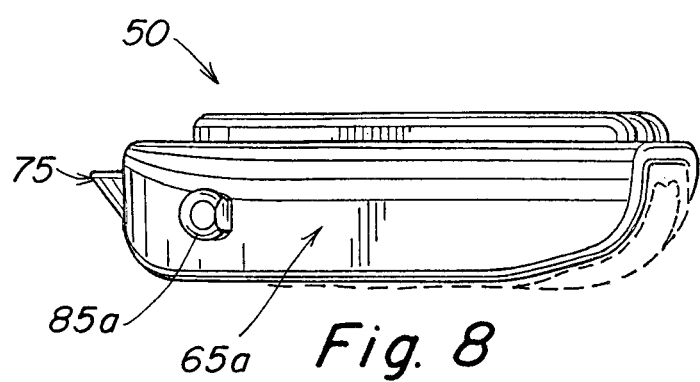
FIG. 8 is a right side elevational view of a lower tray, the left side being a mirror image thereof.
Figure 9:
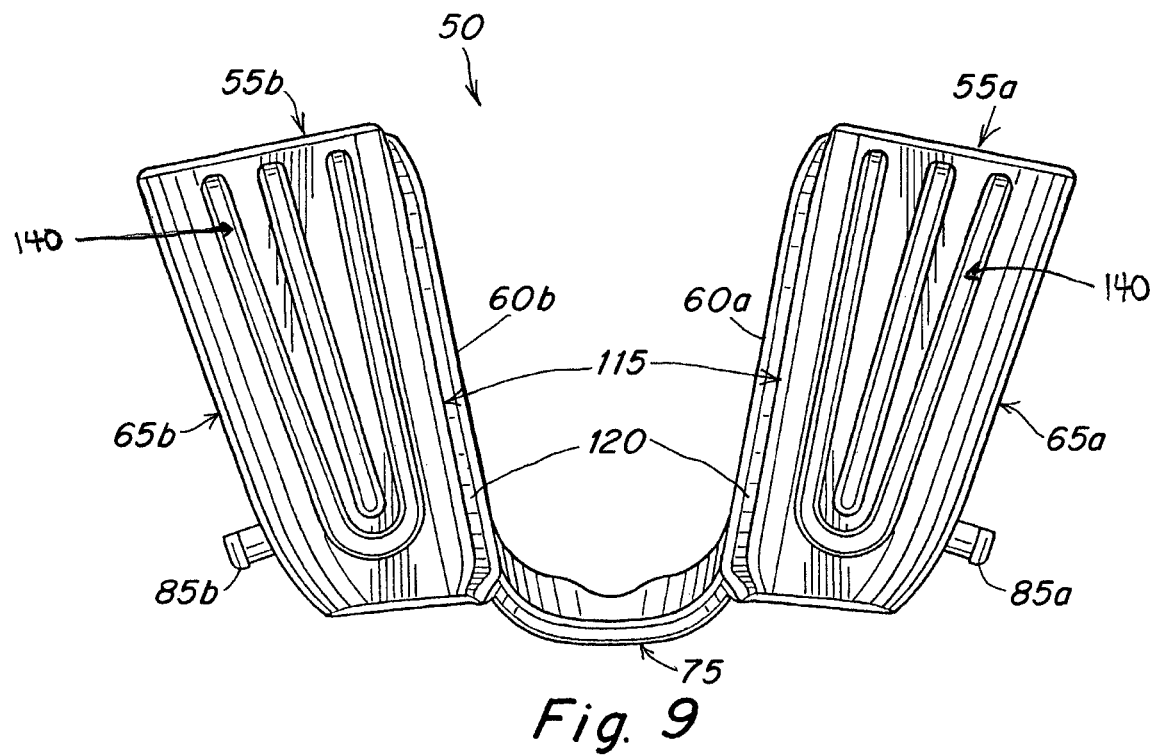
FIG. 9 is a top plan view of a lower tray.
Figure 10:
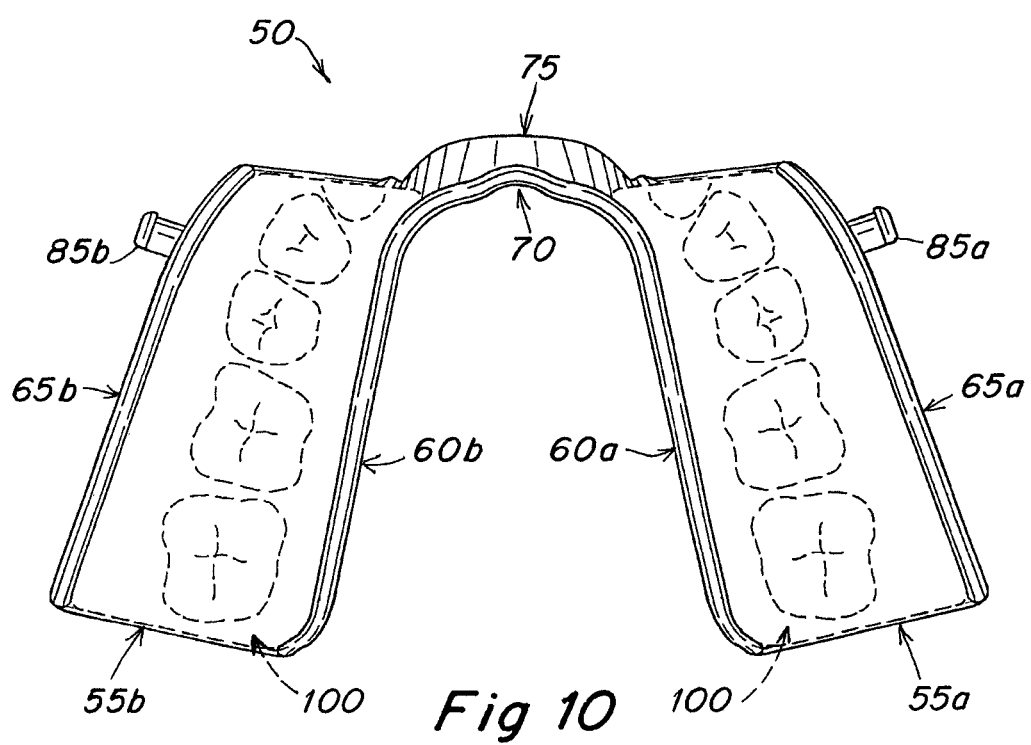
FIG. 10 is a bottom plan view of a lower tray.

FIGS. 6-11 show views of lower tray 50, which includes first lower section 55a, on which first lower inner wall 60a and first lower outer wall 65a are positioned. Similarly, second lower section 55b includes second lower inner wall 60b and second lower outer wall 65b. Lower bridge 75 connects first lower section 55a to second lower section 55b. Also seen in FIGS. 6, 8, 9, 10, and 11 is first lower post 85a, on the outer anterior portion of the first lower section, and second lower post 85b, on the outer anterior portion of the second lower section. Seen in FIGS. 6, 7, and 10 is notch 70 on lower bridge 75, which provides space to avoid interference or irritation of the lingual frenulum.

In another embodiment, the orientation of the posts 80a and 80b, in conjunction with posts 90a and 90b, may be reversed, such that posts 80a and 80b are positioned near the posterior of upper tray 10, and posts 90a and 90b are positioned near the anterior portion of lower tray 50.

Figure 16:
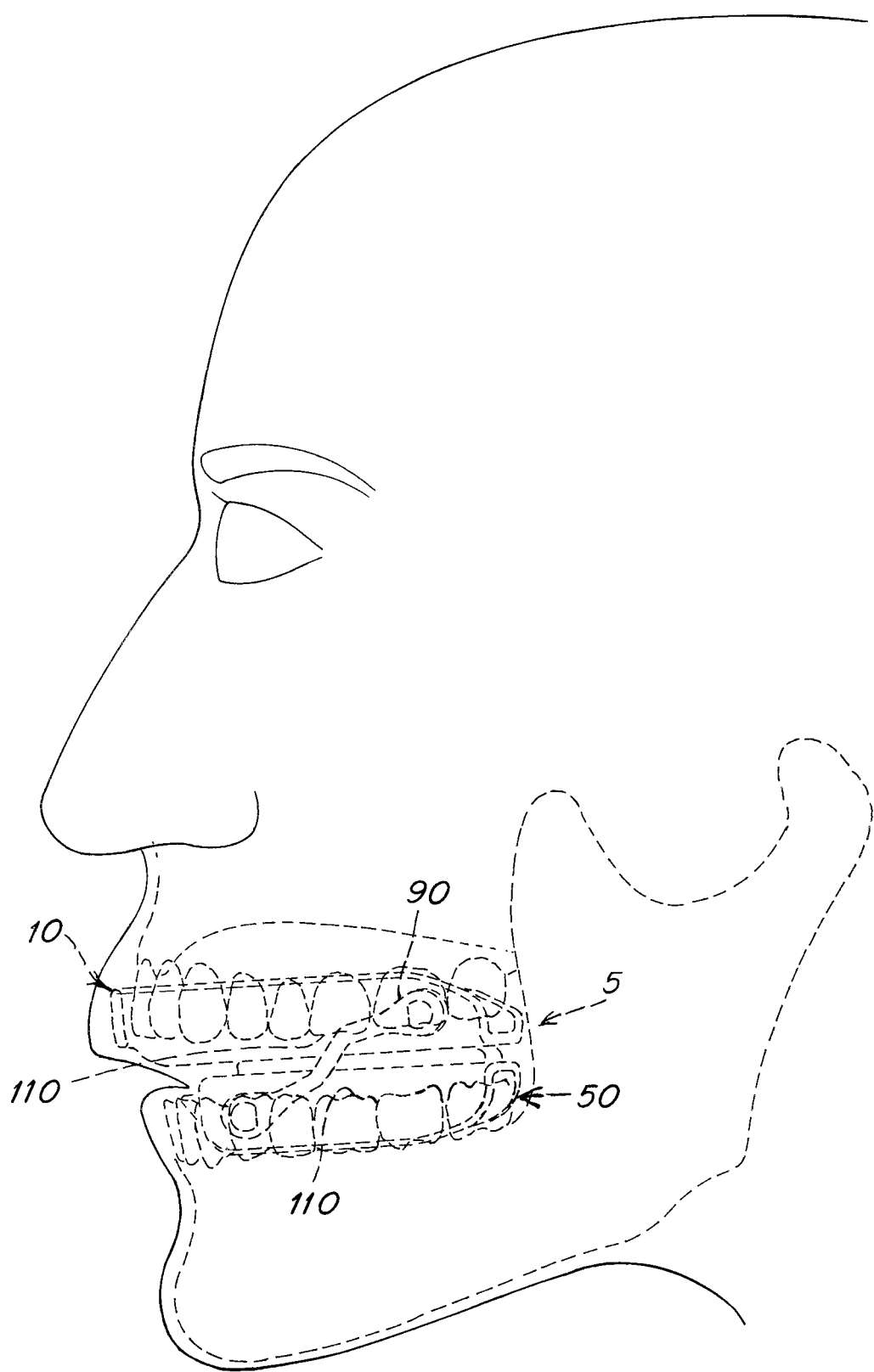
FIG. 16 shows a right-side view of an oral appliance in the mouth of a user.

Both upper tray 10 and lower tray 50 may include thermal impression material 100 on the planar surfaces of the first upper section 15a, second upper section 15b, first lower section 55a, and second lower section 55b. As seen in FIG. 16, thermal impression material 100 may engage with dorsal dental surfaces 110, to form impressions of a user's teeth. Material 100 may be ethylene vinyl acetate that is moldable when boiled and provides the ability to conform the device to the individual's teeth, with other materials also suitable for use.

A thermal impression system such as this may be referred to as a "boil-and-bite" device, meaning that it requires some advance preparation to fit the device by heating the device trays in boiling water, with an individual biting into the softened thermal impression material to set the device to the individual's teeth.

Typical preparation may require an individual to boil water and place each appliance tray in the boiling water for 3 minutes 30 seconds. Thereafter, when the device is removed from the hot water and has cooled down for about 15 seconds, the individual inserts the device into the mouth, pressing the tray over the teeth then biting down to set the teeth firmly into the impression material and tray. The process starts with fitting an upper tray such as upper tray 10, then repeating the process to fit a lower tray, such as lower tray 50. While the thermal impression material 100 is still soft and moldable the excess thermal impression material may be pressed onto the exposed teeth and gums with fingers for improved fit and retention. The device may be reheated several times as necessary to complete the fitting process. The individual may also remove any excess thermal impression material that could lead to discomfort or irritation.

Figure 12:
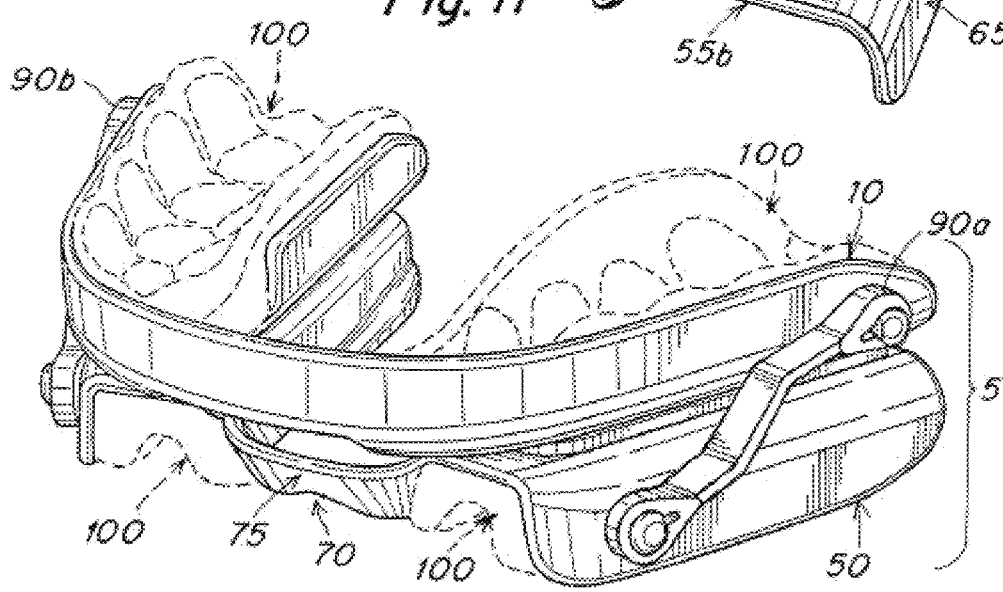
FIG. 12 is a top, front, right side perspective view of an upper tray and a lower tray with side straps of an oral appliance.

An assembled oral appliance 5 is seen in FIG. 12, with first side strap 90a removably connecting first upper post 80a to first lower post 85a; and second side strap 90b removably connecting second upper post 80b to second lower post 85b. Each side strap 90a and 90b may have holes at each end that fit securely over the posts 85a, 85b, 90a, and 90b. Therefore, side straps 90a and 90b removably connect upper tray 10 with lower tray 50. The side straps are a paired set that are identical in length to one another.

In an embodiment in which oral appliance 5 is used for the purpose of mandibular advancement, side straps 90 create offset between upper tray 10 and the lower tray 50, with the length of the straps correlating with the amount of mandibular advancement desired, or an individual's optimal bite. FIG. 13 shows side straps 90 in three different exemplary lengths. Longer straps provide more offset between upper tray 10 and lower tray 50, and therefore more mandibular advancement, than shorter straps, thereby creating variable offset for the oral appliance. In one embodiment, ten different straps provide an adjustment range of 10 millimeters, in one-millimeter increments. Another embodiment simplifies the number of advancement options to three advancement positions based on the type of the user's bite: normal, under bite, overbite. Of course, more than 10 different strap lengths may be employed, or fewer than three.

Figure 11:
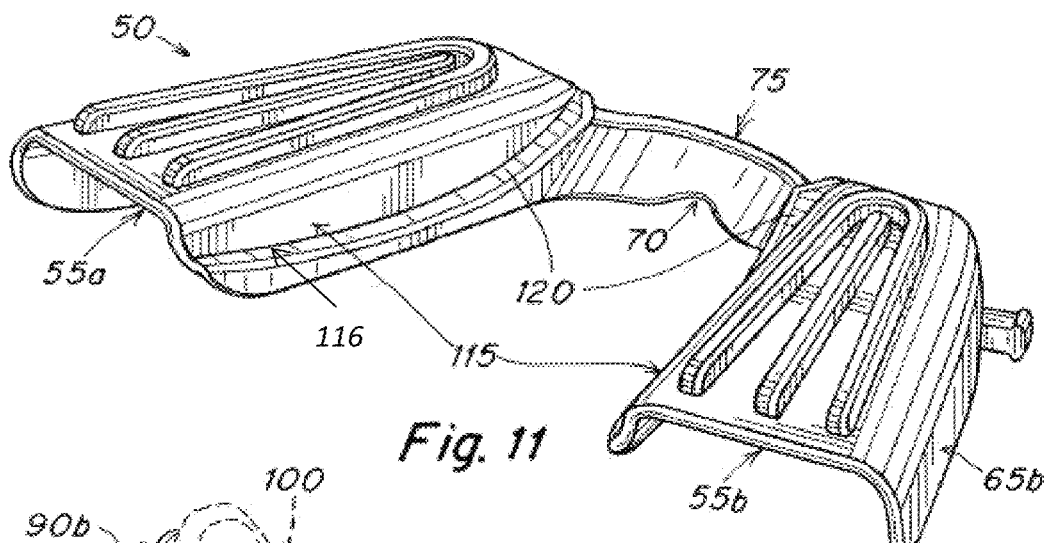
FIG. 11 is top, rear, right side perspective view of a lower tray.

FIG. 11 shows lingual surfaces 115 on both the first lower section 55a and second lower section 88b. Lingual ramp 120 includes an inclined surface, which slopes particularly near the anterior portion of lower tray 50. Lingual ramps 120 protrude just slightly so that they rest under the outermost sides of a user's tongue. Lingual ramps 120 may facilitate and promote the upward and forward movement of the tongue to prevent the tongue from collapsing into the throat and restricting airflow in the upper airway. Also seen in FIG. 11 as well as FIG. 12, the profile of lower bridge 75 may match the slope of lingual ramp 120, so that the similarly-sloped surfaces work together promote the desired forward and upward tongue movement.

A related benefit is the open section 35, and seen in FIGS. 4 and 5, which also may provide space for the tongue to come forward so as to not fall back in the throat and constrict the airway. Open section 50 is enabled by the open anterior configurations of both lower tray 50 and upper tray 10.

Within upper tray 10, open section 35 is present by connecting first upper section 15a to second upper section 15b only via upper outer wall 25. This forms a continuous U-shaped outer wall, with no connection between the planar portions of first upper section 15 and second upper section 15b. Similarly, first upper inner wall 20a and second upper inner wall 20b are not connected in the anterior area, which also enables the open section 35. Within lower tray 50, open section 35 is present by connecting first lower section 55a to second lower section 55b only via lower bridge 70. Herein, there may be no portion of lower tray 50 in the overall anterior portion of oral appliance 5, with lower bridge 75 being the forwardmost portion of lower tray 50.

The resulting combination of the anterior portions of both upper tray 10 and lower tray 50, along with the configuration of joining the first and second sections of each, create the open section 50.

Figure 14:
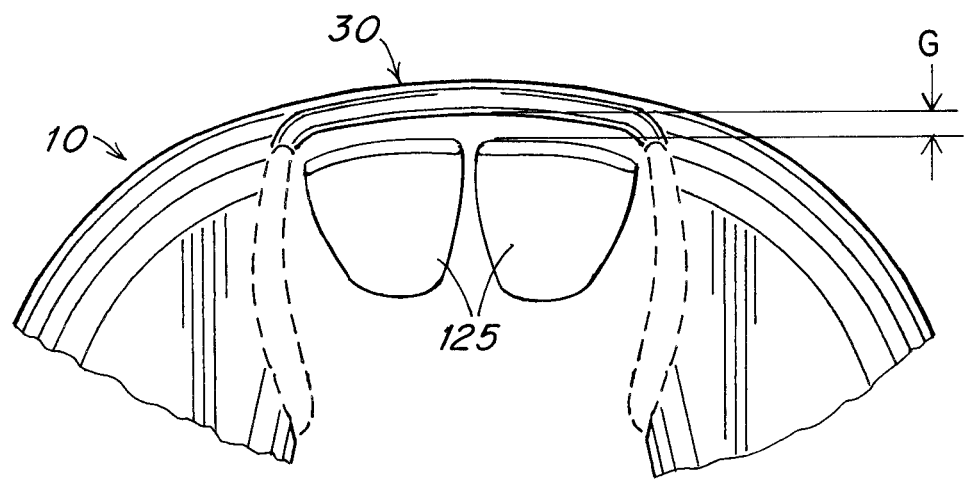
FIG. 14 shows the clearance between the outer wall of the upper tray and the anterior maxillary teeth.
Figure 15:
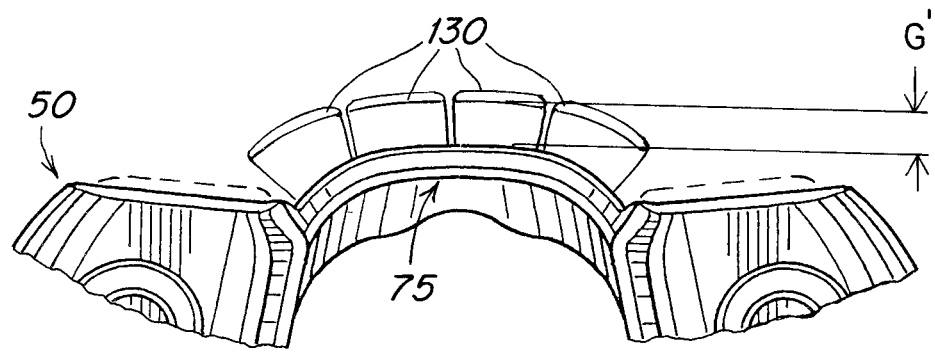
FIG. 15 shows the clearance between the lower bridge of the lower tray and the anterior mandibular teeth.

FIG. 14 and FIG. 15 show an embodiment in which the oral appliance does not contact the anterior dentition. This aspect of this embodiment serves to reduce the pressure exerted on the anterior teeth and any resulting tooth discomfort that may be associated with the forces generated on the front teeth when using mandibular advancement devices.

FIG. 14 shows a space, or clearance, between anterior maxillary teeth 125 and upper outer wall 25. Similarly, FIG. 15 shows a space, or clearance, between anterior mandibular teeth 130 and lower bridge 75. In FIG. 14 sections 15a and 15b of upper tray 10 are joined by anterior bridge 30, with the inner surface (that is, the side of anterior bridge 30 facing the teeth) of anterior bridge 30 exterior tray wall positioned just in front of the upper front teeth below the superior labial frenulum. In FIG. 15, sections 55a and 55b of lower tray 50 are joined by lower bridge 75, with the outer surface (that is, the side of lower bridge 75 facing the teeth) of lower bridge 75 angled and positioned behind the lower front teeth just above the sublingual surface.

An embodiment of oral appliance 5 is therefore able to create mandibular advancement without contacting the maxillary teeth. Instead of applying pressure to the anterior teeth to create the forward force needed to advance the mandible, this embodiment relies at least in part on the friction between a user's buccal teeth and the molded surface of thermal impression material 100. That is, upper tray 10 and lower tray 50 may be incapable of significant fore-after movement relative to the teeth, as the molded surface of thermal impression material 100 keeps them fixed in position on a user's buccal teeth. With each tray fixed in position, side straps 90a and 90b then position the trays relative to each other.

In other embodiments, there may be several additional elements to widen a user's airway to improve airflow and device performance. One such element may be platform 140 on the upper surface of the lower tray 50 which contacts the lower surface of the upper tray 10. Platform 140 creates additional vertical distance between the upper and lower teeth to increase the dilation of the upper airway. One embodiment uses a platform height of 0.08 inches. This distance may be reduced by filing or similar methods if less vertical separation is needed. In an alternate embodiment, platform 140 may be positioned on the lower surface of the upper tray 10 which contacts lower tray 50.

Although the present system has been described with respect to one or more embodiments, it will be understood that other embodiments of the present system may be made without departing from the spirit and scope of the present system. Hence, the invention is deemed limited only by claims and the reasonable interpretation thereof.

The invention claimed is:

1. An oral appliance, comprising:
   an upper tray with a first upper section, a second upper section, a first upper inner wall, a second upper inner wall, an upper outer wall;
   an anterior bridge connecting the first upper section to the second upper section, creating an open section between the first upper section and the second upper section;
   a lower tray separate from the upper tray, with a first lower section, a second lower section, a first lower inner wall, a second lower inner wall, a first lower outer wall, a second lower outer wall;
   a lower bridge connecting the first lower section to the second lower section;
   a first upper post located the first upper section;
   a second upper post located on the second upper section;
   a first lower post located on the first lower section;
   a second lower post located on the second lower section;
   a first side strap removably connecting the first upper post to the first lower post;
   a second side strap removably connecting the second upper post to the second lower post, the first and second side straps a paired set identical in length to one another, in which mandibular advancement is variable by swapping the paired set of first and second side straps for a different length paired set of first and second straps, the different length strap pairs further enabling the anterior bridge and lower bridge to be spaced apart from a user's anterior maxillary teeth, anterior mandibular teeth, and adjacent anterior gum tissue when the oral appliance is positioned in a user's mouth;
   a thermal impression material on a surface that faces dorsal dental surfaces of each of the first upper section, the second upper section, the first lower section, the second lower section; and
   in which the first lower section and second lower section each include a lingual surface designed to engage a user's tongue.

2. The oral appliance of claim 1, in which the lingual surfaces of the first lower section and the second lower section further each include a lingual ramp with an inclined surface.

3. The oral appliance of claim 2, in which the lower bridge is ramped to match and connect the inclined surface of the lingual ramps on the first lower section and the second lower section.

4. The oral appliance of claim 3, in which a slope of the lingual ramp of the first lower section a slope of the lingual ramp of the second lower section and a slope of the ramped lower bridge are configured to promote forward and upward movement of a user's tongue.

5. The oral appliance of claim 2, in which the lower bridge is ramped to connect and match a slope of the inclined surface of the lingual ramps on the first lower section and the second lower section, the lower bridge's ramped surface configured non coplanar to the inclined surfaces of the lingual ramps.

6. The oral appliance of claim 2, in which the lingual ramps are configured at least partially non coplanar relative to a planar surface of the lower tray.

7. The oral appliance of claim 2, in which a posterior portion of the inclined surface of each lingual ramp slopes downward to a mid-portion of each ramp, and an anterior portion of the inclined surface of each lingual ramp slopes downward to the mid-portion of each ramp.

8. The oral appliance of claim 1, in which the first upper post is located on a first outer posterior portion of the first upper section; the second upper post is located on a second outer posterior portion of the second upper section; the first lower post is located on a first outer anterior portion of the first lower section; and the second lower post is located on a second outer anterior portion of the second lower section.

9. The oral appliance of claim 1, in which the first upper post is located on a first outer anterior portion of the first upper section; the second upper post is located on a second outer anterior portion of the second upper section; the first lower post is located on a first outer posterior portion of the first lower section; and the second lower post is located on a second outer posterior portion of the second lower section.

10. The oral appliance of claim 1 in which the oral appliance is configured to advance a user's mandible.

11. The oral appliance of claim 1, in which the open section is designed into the oral appliance's anterior portion by both the lower tray and the upper tray having open anterior portions.

12. The oral appliance of claim 1, in which a platform on an upper surface of the lower tray creates a vertical space between the upper tray and the lower tray.

13. The oral appliance of claim 1, in which a platform on a lower surface of the upper tray creates a vertical space between the upper tray and the lower tray.

14. The appliance of claim 1, in which the first and second side straps each have a non-linear shape along their major axis.

15. The oral appliance of claim 1, in which a platform on a lower surface of the upper tray or a platform on an upper surface of the lower tray is configured as three ridges that form a W shape, the ridges' height being 0.08 inches.

16. An oral appliance, comprising:
  an upper tray with a first upper section, a second upper section, a first upper inner wall, a second upper inner wall, an upper outer wall;
  an anterior bridge connecting the first upper section to the second upper section, creating an open section between the first upper section and the second upper section;
  a lower tray separate from the upper tray, with a first lower section, a second lower section, a first lower inner wall, a second lower inner wall, a first lower outer wall, a second lower outer wall;
  a lower bridge connecting the first lower section to the second lower section;
  a first upper post located the first upper section;
  a second upper post located on the second upper section;
  a first lower post located on the first lower section;
  a second lower post located on the second lower section;
  a first side strap removably connecting the first upper post to the first lower post;
  a second side strap removably connecting the second upper post to the second lower post, the first and second side straps a paired set identical in length to one another;
  a thermal impression material on a surface that faces dorsal dental surfaces of each of the first upper section, the second upper section, the first lower section, the second lower section; and
  in which the first lower section and second lower section each include a lingual surface designed to engage a user's tongue, the lingual surface of the first lower section and the lingual surface of second lower section each comprising a lingual ramp with an inclined surface, the lingual ramps both configured at least partially non coplanar relative to a planar surface of the lower tray, with an indentation created by the non-coplanar configuration capable of guiding a user's tongue.

17. The oral appliance of claim 16, in which the lower bridge is ramped to match and connect the inclined surface of the lingual ramps on the first lower section and the second lower section.

18. The oral appliance of claim 16, in which a slope of the lingual ramp of the first lower section a slope of the lingual ramp of the second lower section and a slope of the ramped lower bridge are configured to promote forward and upward movement of a user's tongue.

19. The oral appliance of claim 16, in which the oral appliance is configured to advance a user's mandible.

20. The oral appliance of claim 16, in which the open section is designed into the oral appliance's anterior portion by both the lower tray and the upper tray having open anterior portions.

21. The oral appliance of claim 16, in which the lower bridge is ramped to connect and match a slope of the inclined surface of the lingual ramps on the first lower section and the second lower section, the lower bridge's ramped surface configured non coplanar to the inclined surfaces of the lingual ramps.

* * * * *